(12) United States Patent
Neffgen et al.

(10) Patent No.: US 12,186,416 B2
(45) Date of Patent: Jan. 7, 2025

(54) MONOMER MIXTURE FOR PRODUCING A DENTAL MATERIAL

(71) Applicant: MÜHLBAUER TECHNOLOGY GMBH, Hamburg (DE)

(72) Inventors: Stephan Neffgen, Pinneberg (DE); Swen Neander, Hamburg (DE)

(73) Assignee: MÜHLBAUER TECHNOLOGY GMBH, Hamburg (DE)

( * ) Notice: Subject to any disclaimer, the term of this patent is extended or adjusted under 35 U.S.C. 154(b) by 0 days.

(21) Appl. No.: 18/565,442

(22) PCT Filed: May 13, 2022

(86) PCT No.: PCT/EP2022/063002
§ 371 (c)(1),
(2) Date: Nov. 29, 2023

(87) PCT Pub. No.: WO2022/253551
PCT Pub. Date: Dec. 8, 2022

(65) Prior Publication Data
US 2024/0238167 A1 Jul. 18, 2024

(30) Foreign Application Priority Data
May 31, 2021 (DE) ............... 10 2021 113 969.4

(51) Int. Cl.
| C08F 2/46 | (2006.01) |
| *A61K 6/50* | (2020.01) |
| *A61K 6/891* | (2020.01) |
| C08F 2/50 | (2006.01) |
| C08G 61/04 | (2006.01) |

(52) U.S. Cl.
CPC ............. *A61K 6/891* (2020.01); *A61K 6/50* (2020.01)

(58) Field of Classification Search
CPC ... C08F 2/46; C08F 2/50; A61K 6/891; A61K 6/50; C08G 60/04
USPC ....... 522/182, 178, 1, 6, 71, 189, 184; 520/1
See application file for complete search history.

(56) References Cited

U.S. PATENT DOCUMENTS

| 6,730,156 | B1 | 5/2004 | Windisch et al. | |
| 2007/0299154 | A1* | 12/2007 | Dersham | C08G 63/916 526/260 |
| 2012/0082959 | A1 | 4/2012 | Blomker et al. | |
| 2015/0080490 | A1 | 3/2015 | Burtscher et al. | |
| 2018/0265527 | A1 | 9/2018 | Moszner et al. | |
| 2020/0121564 | A1 | 4/2020 | Matsuo et al. | |
| 2020/0157267 | A1* | 5/2020 | Shimoju | C08F 2/50 |
| 2021/0267849 | A1 | 9/2021 | Hahn et al. | |

FOREIGN PATENT DOCUMENTS

| DE | 2816823 A1 | 10/1978 |
| EP | 0104491 A1 | 4/1984 |
| EP | 3153150 A1 | 4/2017 |
| GB | 1576080 A | 10/1980 |
| GB | 2291053 A1 | 1/1996 |
| JP | 2016030764 A | 3/2016 |

OTHER PUBLICATIONS

Vaidyanathan et al, Visible light cure characteristics of a cycloaliphatic polyester dimethacrylate alternative oligomer to bisGMA, 2015, 1(2-4), 59-65 (Year: 2015).*
International Search Report and Written Opinion mailed Aug. 29, 2022, International Application No. PCT/EP2022/063002, 15 pages.
Vaidyanathan et al., "Affiliations Visible light cure characteristics of a cycloaliphatic polyester dimethacrylate alternative oligomer to bisGMA" Acta Biomater Odontol Scand. Sep. 18, 2015;1(2-4):59-65.
Söderholm et al., "BIS-GMA—based resins in dentistry: are they safe?" J Am Dent Assoc. Feb. 1999; 130(2):201-9.

* cited by examiner

*Primary Examiner* — Jessica Whiteley
(74) *Attorney, Agent, or Firm* — Casimir Jones, S.C.; Anne M. Reynolds

(57) ABSTRACT

The invention relates to a monomer mixture for producing a dental material comprising: a. at least one base monomer M1 of the following formula 1: PG-S-A-S—[OOC—K—COO—S-A-S]$_n$-PG (formula 1), where PG=a polymerizable group selected from OOC—CH=CH$_2$ and —OOC—C(CH$_3$)—CH$_2$; S=a spacer group selected from an unbranched and a branched alkylene, which has C1-C10 carbon atoms and which can also contain oxygen or —OOC— in the carbon chain, or S is omitted; A=an aliphatic polycyclic group; K=an aliphatic acyclic or cyclic saturated or unsaturated unit with C1-C10 carbon atoms; and n=1-9; b. at least one base monomer M2 of the following formula 2: PG'—S'-A'—S'—PG' (formula 2), where PG'=a polymerizable group selected from OOC—CH=CH$_2$ and —OOC—C(CH$_3$)=CH$_2$; S'=a spacer group selected from an unbranched and a branched alkylene, which has C1-C10 carbon atoms and which can also contain oxygen or —OOC— in the carbon chain, or S' is omitted; and A'=an aliphatic polycyclic group, wherein the mass ratio Y=m(M2)/m(M1) of the base monomers M2 to M1 is $0.9 \leq Y \leq 20$. The invention also relates to the use of the monomer mixture, to a polymerizable dental material containing such a monomer mixture, to a polymerizable dental material for use in a therapeutic method, and to a cured dental material.

20 Claims, No Drawings

MONOMER MIXTURE FOR PRODUCING A DENTAL MATERIAL

The invention relates to a monomer mixture for producing a dental material, to a use of the monomer mixture, to a polymerizable dental material comprising such a monomer mixture, to a polymerizable dental material comprising such a monomer mixture for use in a therapeutic method, and to a cured dental material.

Radically polymerizable dental materials contain principally (meth)acrylate monomers. For restorative and prosthetic dental materials, such as dental fillings and dental prostheses, dimethacrylate systems are usually used, on account of their properties, such as quick radical polymerization, good mechanical properties and esthetic appearance. Customary base monomers are linear aliphatic or aromatic group-containing structures having terminal methacrylate functionalities which have a high molecular weight, such as 2,2-bis[4-(2-hydroxy-3-methacryloxypropoxy)phenyl]propane (bisGMA) and 7,7,9-trimethyl-4,13-dioxo-3,14-dioxa-5,12-diazahexadecane-1,16-diyl bis(2-methylacrylate) (UDMA).

Efforts have been made for some time to very largely do without the use of bisGMA and to replace it at least partly with other compounds. The focus here is primarily on urethane monomers and urethane oligomers. The most commercially widespread compound for at least partial replacement of bisGMA in the dental materials sector is UDMA.

Base monomers, such as bisGMA and UDMA, despite being included in wide ranges of commercial radically polymerizable dental materials, have certain disadvantages. In general they are substances of high viscosity or solids. For this reason, mixtures with monomers of substantially low viscosity, such as triethylene glycol dimethacrylate (TEGDMA), are used. TEGDMA is a very flexible, low molecular weight monomer having a low viscosity (of 0.01 Pa s) which during the polymerization has a high mobility, so promoting the polymerization conversion.

These monomer mixtures and the dental materials obtained from them, however, have certain problematic properties, which may be detrimental to their success in clinical treatment. For example, monomer mixtures of these dimethacrylate monomers exhibit relatively low polymerization conversion, severe polymerization shrinkage, poor toughness, and unwanted absorption of water. The known systems are often only able to achieve a comparatively low conversion of the double bonds, which not only contributes to inadequate mechanical properties and inadequate wear resistance but is also a disadvantage for the toxicology and biocompatibility of the polymerized dental materials. Furthermore, the volume shrinkage of the dimethacrylate monomers presently used and the shrinkage stresses of a dental filling may lead to failure of the bond between tooth and filling, leading to microleakages and consequently to secondary caries; in turn, this may considerably reduce the longevity of the restoration. Attempts to increase the double bond conversion in order to reduce unconverted monomers unfortunately lead to an increase in polymerization shrinkage and shrinkage stress.

Low molecular weight monomers with oligo[ethyleneoxy]groups, such as TEGDMA, which exhibit a certain water-solubility and hence bioavailability, are now being rated critically because of their toxicological properties and also their sensitivity toward processes of biodegradation. Also rated critically are monomers with the structural element bis-2,2-[p-oxyphenyl]propane, i.e., monomers based on bisphenol A, since dental materials comprising monomer mixtures with these structure elements have been found to release detectable quantities of bisphenol A, to which toxicologically critical properties are ascribed.

There are various approaches to increasing the conversion and/or reducing the volume shrinkage. In the case of dental composites for dental fillings that comprise filler in an organic resin matrix, attempts are made to reduce the volume shrinkage by raising the filler content. If the filler content is too high, however, it is difficult to mix the fillers with the organic resin. There is also a limit on the filler content for dental composites, which must have a certain fluidity. For increasing the conversion and reducing the polymerization shrinkage, moreover, new monomers are being developed, examples being urethane methacrylate monomers with high molecular weights. The synthesis of these monomers is costly and complicated and typically necessitates purification steps as well, making such monomers limited in their availability. For a given functionality of the monomers, raising the molecular weight generally entails a deterioration in the mechanical properties of the cured dental materials. Moreover, the elevated viscosity of such monomers means that they must be used with relatively high quantities of low-viscosity monomers, to allow them to be used for dental composites, and this has adverse consequences for the shrinkage.

EP 2436365 B1 describes low-shrinkage dental composites comprising monomer mixtures which contain the monomers (b1) and (b2) in a ratio of 1:20-5:1. The example compositions contain in each case 4.8-76.6% by weight of bis((meth)acryloyloxymethyl)tricyclo[5.2.1.0$^{2,6}$]decane (b1), 90.9-19.1% by weight of UDMA (b2) and 4.3% by weight of TEDMA (b2). Independently of the ratio of (b1) to (b2), these composites have a polymerization shrinkage of about 1.50%. If, as in comparative example 11, the filler fraction is reduced and the fraction of TEDMA is increased, there is an increase in the polymerization shrinkage.

Vaidyanathan et al., Visible light cure characteristics of a cycloaliphatic polyester dimethacrylate alternative oligomer to bisGMA; Acta Biomater Odontol Scand. 2015; 1:59-65, disclose the use of PEM-665 as a BPA-free alternative to bisGMA in combination with 30% or 50% by weight of TEGDMA. The polymerization conversions of these mixtures have been studied, with the combinations of PEN with TEGDMA having a higher percentage polymerization conversion than the combinations of bisGMA with TEGDMA.

There is therefore the need for monomers and monomer mixtures which are capable of enabling reduced toxicity potential and reduced volume shrinkage while at the same time enabling good mechanical properties for the dental material to be produced from them and which are easily obtainable.

The object of the present invention is therefore to provide a monomer mixture which overcomes the disadvantages set out above for the prior art and which in particular enables production of dental materials, especially dental composites, with improved volume shrinkage and improved flexural strength.

The invention achieves this object by means of a monomer mixture for producing a dental material, comprising:
  a. At Least One Base Monomer M1 of the Following Formula 1:

(formula 1)

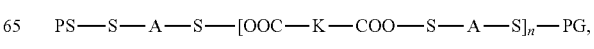

where
PG=a polymerizable group selected from OOC—CH=CH$_2$ and —OOC—C(CH$_3$)=CH$_2$;
S=a spacer group selected from unbranched and branched alkylene with C1-C10 carbon atoms that may additionally
contain oxygen and/or —OOC— in the carbon chain, preferably methylene,
or S is absent;
A=an aliphatic polycyclic group, preferably an aliphatic tricyclic hydrocarbon group, in which one or more hydrogen atoms may be replaced each independently of one another by C1-C4 alkyl radicals, C1-C4 alkoxy radicals, fluorine atoms, chlorine atoms or trifluoromethyl groups, more preferably tricyclodecanylene, more preferably still tricyclo[5.2.1.0/2,6]decanylene;
K=an aliphatic acyclic or cyclic, saturated or unsaturated unit with C1-C10 hydrocarbon, preferably with C3-C10 hydrocarbon, more preferably a saturated cycloaliphatic unit, more preferably still 1,4-cyclohexanylene;
n=1-9, preferably 1-5, more preferably 1-4;
b. At Least One Base Monomer M2 of the Following Formula 2:

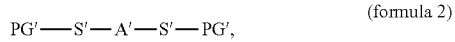
(formula 2)

where
PG'=a polymerizable group selected from OOC—CH=CH$_2$ and —OOC—C(CH$_3$)=CH$_2$;
S'=a spacer group selected from unbranched and branched alkylene with C1-C10 carbon atoms that may additionally contain oxygen and/or —OOC— in the carbon chain, preferably methylene,
or S' is absent;
A'=an aliphatic polycyclic group, an aliphatic tricyclic hydrocarbon group, in which one or more hydrogen atoms may be replaced each independently of one another by C1-C4 alkyl radicals, C1-C4 alkoxy radicals, fluorine atoms, chlorine atoms or trifluoromethyl groups, more preferably tricyclodecanylene, more preferably still tricyclo[5.2.1.0/2,6]decanylene;
where a mass ratio Y=m(M2)/m(M1) of the base monomers M2 to M1 is $0.9 \leq Y \leq 20$, preferably $0.9 \leq Y \leq 10$, more preferably $0.95 \leq Y \leq 3$.

Preferred embodiments can be found in the dependent claims.

A number of terms used in the context of the invention will first be elucidated.

Polymerizable dental materials are understood in accordance with the invention to be materials for (bio)medical use, especially on hard tooth substance, such as enamel and dentine, or on bony tissue, such as on the jawbone.

The polymerizable dental material is generally a resin-based material which is a mixture of different constituents that is curable. In the context of this invention, a resin consists substantially of the monomer mixture and of further constituents soluble in the monomers, such as, for example, initiators, stabilizers, etc.

In the context of the present invention, a monomer mixture is a mixture which comprises base monomers M1 and M2 and also, optionally, base monomers M3 and/or other monomers of the polymerizable dental material. Further constituents of the polymerizable dental material, such as initiator, filler, customary dental additive, etc., are not constituents of the monomer mixture.

In the context of the present invention, base monomer M1 comprises monomers if n=1 and oligomers if n=2 to 9. Monomers and oligomers with n=1 to 9 are presently referred to as base monomers M1.

In the monomer mixture there are preferably two or more base monomers M1, more preferably at least two base monomers M1, more preferably still more than two base monomers M1, even more preferably more than three base monomers M1, even more preferably still more than four base monomers M1.

In one embodiment, all of the base monomers M1 of a monomer/oligomer series with n=1-9, preferably with n=1-5, more preferably with n=1-4, may be present alongside one another. In other words, for n=1-9, there would then be at least 9 compounds present (i.e. one monomer and eight oligomers), for n=1-5 at least 5 compounds (i.e. one monomer and four oligomers) and for n=1-4 at least 4 compounds (i.e. one monomer and three oligomers).

The mass distribution of the base monomers M1 may vary within wide ranges. It may be the case that the base monomers M1 in which n=2-5 or n=2-4 have the highest mass fraction, based on the total mass fraction of the base monomers M1. It may alternatively be the case that the base monomer or monomers M1 with n=1 have the highest mass fraction in comparison to each individual base monomer M1 with n=2-9 that is included in the monomer mixture.

The base monomer M2 may be selected from bis(methacryloyloxymethyl)tricyclo[5.2.1.0/2,6]decane, bis(acryloyloxymethyl)tricyclo[5.2.1.0/2,6]decane and mixtures thereof. More preferably the base monomer M2 is bis(methacryloyloxymethyl)tricyclo-[5.2.1.0/2,6]decane. The base monomer M2 may be a commercially available monomer, such as tricyclo[5.2.1.0/2,6]decanedimethanol diacrylates from Polyscience. The monomers in question may alternatively be monomers obtainable by esterification reaction in accordance, for example, with the preparation examples in EP0235836B1 or U.S. Pat. No. 4,131,729/DE2816823. As a general rule, industrially available base monomers M2 based on tricyclo[5.2.1.0/2,6]decanedimethanol di(meth)acrylate comprise isomer mixtures in which the exocyclic methylene groups are bonded to different framework carbon atoms according to isomer.

The monomer mixture may comprise a base monomer M3 which differs from the base monomers M1 of the formula 1 and M2 of the formula 2.

The base monomer M3 is preferably selected from urethane-based monomers.

Suitable base monomers M3 may be selected from difunctional urethane (meth)acrylates, polyfunctional urethane (meth)acrylates and mixtures thereof.

The base monomer M3 preferably comprises urethane di(meth)acrylates. Preferred are urethane di(meth)acrylates selected from linear or branched, alkylene-functionalized urethane di(meth)acrylates and urethane di(meth)acrylate-functionalized polyethers.

Preference is given to difunctional urethane (meth)acrylates which are selected from difunctional urethane (meth)acrylates with divalent alkylene group and also from those with divalent cyclic aliphatic hydrocarbon group. Such difunctional urethane (meth)acrylates with divalent alkylene group are preferably selected from linear or branched urethane di(meth)acrylates functionalized with a divalent alkylene group, urethane di(meth)acrylate-functionalized polyethers with alkylene group(s), such as bis(methacryloxy-2-ethoxycarbonylamino)alkylene, bis(methacryloxy-2-ethoxycarbonylamino)-substituted polyalkylene ethers. Preference is given to bis(methacryloxy-2-ethoxycarbonylamino)alkylenes which comprise linear or branched alkylene groups with C3 to C20, preferably C3 to C9. Particular preference is given to an alkylene substituted by methyl groups. The divalent alkylene preferably comprises 2,2,4-trimethylhexamethylene and/or 2,4,4-trimethylhexamethylene.

The base monomer M3 may, moreover, also be a reaction product of 3-hydroxypropyl methacrylate and trimethylhexamethylene diisocyanate, or a reaction product of 3-hydroxypropyl acrylate and trimethylhexamethylene diisocyanate.

Urethane (meth)acrylates with divalent cyclic aliphatic hydrocarbon group are accessible through reaction of 2 mol of 2-hydroxyethyl methacrylate (HEMA) or 2 mol of 2-hydroxyethyl acrylate (HEA) with 1 mol of cyclic aliphatic diisocyanate. Suitable diisocyanates are isophorone diisocyanate (1-isocyanato-3-isocyanatomethyl-3,5,5-trimethylcyclohexane) or H12-MDI (1-isocyanato-4-[(4-isocyanatocyclohexyl)methyl]cyclohexane and also other cyclic diisocyanates. Examples thereof are the reaction product of 2 molecules of 2-hydroxyethyl acrylate (HEA) and one molecule of isophorone diisocyanate (IPDI), and the adduct of 2 molecules of 2-hydroxyethyl methacrylate (HEMA) and one molecule of isophorone diisocyanate.

Suitable base monomers M3 are available, for example, under the following trade or brand names: Ebecryl 230 (aliphatic urethane diacrylate), Actilane 9290, Craynor 9200 (di-urethane acrylate oligomer), Ebecryl 210 (aromatic urethane diacrylate oligomers), Ebecryl 270 (aliphatic urethane diacrylate oligomer), Actilane 165, Actilane 250, Photomer 6210 (aliphatic urethane diacrylate), Photomer 6623 (hexafunctional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate), Genomer 4256, Genomer 4267 (urethane acrylates), Genomer 4259 (aliphatic urethane dimethacrylate), RCX 18-059 (aliphatic urethane dimethacrylate), UN 1963CG (aliphatic urethane methacrylate), CN 1993CG (aliphatic urethane methacrylate), PRO 21252 (aliphatic urethane acrylate), H1391 (hydroxypropyl-urethane dimethacrylate), H1391 (urethane dimethacrylate), X851-1066 (urethane dimethacrylate IPDI), X726-000 (PEG 400 extended urethane dimethacrylate), urethane methacrylate 11-70 and urethane methacrylate 14-774.

In one preferred embodiment, the base monomer M3 is selected from 7,7,9-(or 7,9,9-)trimethyl-4,13-dioxo-3,14-dioxa-5,12-diazahexadecane-1,16-diyl bis(2-methylacrylate) (UDMA), 7,7,9-(or 7,9,9-)trimethyl-4,13-dioxo-3,14-dioxa-5,12-diazahexadecane-1,16-diol diacrylate (UDA) and mixtures thereof.

The base monomers may each be included in the following mass fractions, based on the total mass of the monomer mixture:
  base monomer M1 from 2% to 52.5% by weight, preferably from 5% to 52.5% by weight, more preferably from 12.5% to 52.5% by weight;
  base monomer M2 from 23% to 96% by weight, preferably from 47.5% to 95.5% by weight, more preferably from 47.5% to 87.5% by weight;
  base monomer M3 from 0% to 50% by weight, preferably from 0.1% to 30% by weight, more preferably from 1% to 15% by weight.

It is preferred for the monomer mixture to comprise or consist of the base monomers M1 and M2 in a mass fraction of 25% by weight or more, more preferably of 50% by weight or more, even more preferably of 70% by weight or more, further preferably of 85% by weight or more, more preferably still of 100% by weight, based on the total masses of the monomer mixture.

The monomer mixture may comprise or consist of the base monomers M1, M2 and M3 in a mass fraction of 95% to 100% by weight, preferably of 99% to 100% by weight, more preferably 100% by weight, based on the total mass of the monomer mixture.

It is preferred in the invention for the monomer mixture not to include any monomer having a bisphenol A structure. In particular there is no 2,2-bis[4-(2-hydroxy-3-(meth)acryloxypropoxy)phenyl]propane (bisGMA) and/or ethoxylated bisphenol A di(meth)acrylate (bisEMA) included. The same applies in respect of the polymerizable dental material.

It is preferred in the invention for the monomer mixture not to include any monomer selected from low molecular weight, low-viscosity mono- and di(meth)acrylates. It is also preferred for no monomer to be included that has a viscosity at a temperature of 23° C.; of less than 0.05 Pa s and/or that has a partial water solubility. In particular, there are no monomers in the monomer mixture that consist of an oligo[ethyleneoxy]group or a linear or branched C1-C10 alkylene group and one or two (meth)acrylate group(s). The monomer mixture is preferably free from hexanediol diacrylate (HDDA), hexanediol dimethacrylate (HDDMA), triethylene glycol diacrylate (TEGDA) and/or triethylene glycol dimethacrylate (TEGDMA). The same applies in respect of the polymerizable dental material.

The viscosity of monomers or of organic resins is usually specified by the manufacturer and may be determined using a viscometer (e.g. Kinexus DSR from Malvern Instruments Ltd.).

The monomer mixture of the invention has a viscosity at a temperature of 23° C.; of preferably 0.2 to 10, more preferably 1 to 6 Pa s.

An advantage of the invention is that the monomer mixture of the invention and hence also the polymerizable dental material of the invention overcome the disadvantages set out above for the prior art. The monomer mixture and the polymerizable dental material may be produced from base monomers which are easily obtainable and which, moreover, have a reduced toxicity potential. The use of the monomer mixture of the invention for producing a dental material results in reduced polymerization shrinkage in conjunction with good mechanical properties in the dental material obtained. With the monomer mixture it is possible in particular to obtain dental materials, more particularly dental composites, which have improved volume shrinkage and improved flexural strength. This is surprising in light of the molecular sizes and structures of the base monomer M1, since the associated expectation would be a reduced crosslinking density and flexural strength.

The monomer mixture and the polymerizable dental material therefore preferably contain no monomers or other compounds with structural elements derived from bisphenol A, and also no low molecular weight mono- and di(meth)acrylates with partial water solubility, in particular, no TEGDMA.

A further subject of the invention is the use of the monomer mixture of the invention, preferably as claimed in any of claims 1 to 10, for producing a radically polymerizable dental material, preferably a dental composite, core buildup, root canal filling, filling, underfilling, securing, crown, bridge, restoration and/or prosthesis material.

A further subject of the invention is also a polymerizable dental material comprising:
   a) the monomer mixture of the invention, preferably as claimed in any of claims 1 to 9;
   b) optionally, at least one initiator or an initiator system for the radical polymerization;
   c) optionally, fillers;
   d) optionally, customary dental additives.

The polymerizable dental material may be constructed in the form of a kit. The kit may comprise one or more components. In the case of the multicomponent kit or system, the dental material is produced immediately before it is used, by mixing the components in the specified proportion and then curing the mixture.

b) Initiator (s)

Suitable initiators or initiator systems are capable of starting off radical polymerization reactions. Such initiators and initiator systems are known to the skilled person.

Initiator systems consist at least of an initiator and at least one further compound, such as a co-initiator, for example. These compounds may be distributed over different components of the polymerizable dental material. The dental material of the invention may be cured thermally, chemically or photochemically, i.e. by irradiation with W and/or visible light.

Photoinitiators are examples of possible suitable initiators. They are characterized in that they are able to bring about curing of the material through an absorption of light in the wavelength range from 300 nm to 700 nm, preferably from 350 nm to 600 nm and more preferably from 380 nm to 500 nm and optionally through the additional reaction with one or more co-initiators. Used preferably here are phosphine oxides, acylphosphine oxides, bisacylphosphine oxides and derivatives thereof, acylgermananes, as described for example in EP2649981A1, WO2017/055209A1 and EP3153150A1, benzoin ethers, benzil ketals, acetophenones, benzophenones, thioxanthones, bisimidazoles, metallocenes, fluorones, $\alpha$-dicarbonyl compounds, aryldiazonium salts, arylsulfonium salts, aryliodonium salts, ferrocenium salts, phenylphosphonium salts or a mixture of these compounds.

Particular preference is given to using diphenyl-2,4,6-trimethylbenzoylphosphine oxide, phenylbis-2,4,6-trimethylbenzoylphosphine oxide, benzoin, benzoin alkyl ethers, benzil dialkyl ketals, $\alpha$-hydroxyacetophenone, dialkoxyacetophenones, $\alpha$-aminoacetophenones, isopropylthioxanthone, camphorquinone, phenylpropanedione, 5,7-diiodo-3-butoxy-6-fluorone, (eta-6-cumene) (eta-5-cyclopentadienyl) iron hexafluorophosphate, (eta-6-cumene) (eta-5-cyclopentadienyl) iron tetrafluoroborate, (eta-6-cumene)(eta-5-cyclopentadienyl)iron hexafluoroantimonate, substituted diaryliodonium salts, triarylsulfonium salts or a mixture of these compounds.

Co-initiators used for photochemical curing are preferably tertiary amines, borates, organic phosphites, diaryliodonium compounds, thioxanthones, xanthene, fluorenes, fluorones, $\alpha$-dicarbonyl compounds, dicarbonyl systems as described in WO2021/048313A1, fused polyaromatics or a mixture of these compounds. Particularly preferred for use are N,N-dimethyl-p-toluolidine, N,N-dialkyl-alkyl-anilines, N,N-dihydroxyethyl-p-toluidine, 2-ethylhexyl p-(dimethylamino)benzoate, ethyl p-(dimethylamino)benzoate, butyrylcholine triphenylbutylborate or a mixture of these compounds.

Initiators used may also include what are called thermal initiators, which are able to bring about curing of the material through the uptake of thermal energy at elevated temperature. Preference in this case is given to the use of inorganic and/or organic peroxides, inorganic and/or organic hydroperoxides, $\alpha,\alpha'$-azobis(isobutyroethyl esters), $\alpha,\alpha'$-azobis(isobutyronitrile), benzopinacols or a mixture of these compounds. Particularly preferred for use are diacyl peroxides such as, for example, benzoyl peroxide or lauroyl peroxide, cumene hydroperoxide, benzopinacol, 2,2'-dimethylbenzopinacol or a mixture of these compounds.

For chemical curing at room temperature, a redox initiator system is generally used that consists of one or of two or more initiator(s) and of one or more co-initiators serving as activator(s). For storage stability reasons, individual components of an initiator system are incorporated into parts of the dental material of the invention that are spatially separate from one another—this means that the material is a multicomponent material, preferably a two-component material. The initiator or initiators used is or are preferably inorganic and/or organic peroxides, inorganic and/or organic hydroperoxides, barbituric acid derivatives, malonylsulfamides, protic acids, Lewis or Broensted acids or compounds releasing such acids, carbenium ion donors such as, for example, methyl triflate or triethyl perchlorate or a mixture of these compounds, and the co-initiator or co-initiators used is or are preferably tertiary amines, heavy metal compounds, especially compounds of groups 8 and 9 of the periodic table ("iron and copper group"), compounds with ionogenically bonded halogens or pseudohalogens, such as, for example, quaternary ammonium halides, weak Broensted acids such as, for example, alcohols and water, or a mixture of these compounds.

The dental material of the invention may also comprise any conceivable combination of the above-described initiators and co-initiators. An example of this are so-called dual-curing dental materials, which contain not only photoinitiators and optionally the corresponding co-initiators for photochemical curing but also initiators and corresponding co-initiators for chemical curing at room temperature.

The polymerizable dental material of the invention is preferably light-curing. In one preferred embodiment, camphorquinone (CQ) included as initiator and 2-ethylhexyl p-(dimethylamino)benzoate (EHA) as co-initiator.

c) Fillers

The polymerizable dental material of the invention may comprise further customary dental additives. The filler particles are not tied to any particular particle shape. Instead, fillers having a spherical, flakelike, plateletlike, acicular, leaflike or irregular form may very well be used. The filler particles preferably have an average particle diameter of 5 nm to 100 μm, more preferably of 5 nm to 50 μm.

Suitable fillers may be selected from a large diversity of materials commonly used in dental products. Through the selection of the filler it is possible to adjust, for example, the fluidity, the viscosity, the consistency, the color, the X-ray-visibility and the mechanical stability of the dental material. On the basis of their chemical nature, the fillers may be divided roughly into three different classes: inorganic fillers, organic fillers, and organic-inorganic composite filler. The fillers may be used not just individually but also in combination with one another.

Inorganic fillers used may comprise ground powders of natural or synthetic glasses or crystalline inorganic substances in various sizes and states (monodisperse, polydisperse). Suitable examples include quartz, cristobalite, glass-ceramic, feldspar, barium silicate glasses (as available for example under the trade names Kimble RAY-SORB T3000, Schott 8235, Schott GM27884, Schott G018-053 and Schott GM39923), barium fluorosilicate glasses, strontium silicate glasses, strontium borosilicate glasses (as available for example under the trade names RAY-SORB T4000, Schott G018-093, Schott G018-163 and Schott GM32087), lithium aluminum silicate glasses, barium glasses, calcium silicates, sodium aluminum silicates, fluoroaluminum silicate glasses (as available for example under the trade names Schott G018-091 and Schott G018-117), zirconium or cesium boroaluminosilicate glasses (as available for example under the trade names Schott G018-307, G018-308 and G018-310), zeolites and apatites. The fillers preferably have a mean particle size d50 of 0.01-15 µm, preferably a mean particle size d50 of 0.2-5 µm and more preferably a mean particle size of 0.2-1.5 µm. It may be preferable for the mean particle size d50 to be between 0.1-0.5 µm. In such cases it is particularly preferable for the mean particle size d90 to be less than 1.0 µm. In addition, discrete, unagglomerated, unaggregated, organically surface-modified nanoparticles may be used, in order to thus produce more uniform filling of the dental material and to increase the hardness and abrasion resistance.

Nanoparticles are understood in this context to be spherical particles having a mean particle size of less than 200 nm. The mean particle size is preferably less than 100 nm and more preferably less than 60 nm. The smaller the nanoparticles, the better able they are to fulfill their function of filling the voids between the coarser particles. The materials for the nanoparticles are preferably oxides or mixed oxides and are more preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. The preferred oxidic nanoparticles are non-agglomerated. In order to facilitate good incorporation of the nanoparticles into the polymer matrix of a composite material, the surfaces of the nanoparticles are organically modified. The fillers are preferably surface-treated with a silanizing agent. A particularly suitable adhesion promoter is methacryloxypropyltrimethoxysilane. Commercially available nanoscale, unagglomerated and unaggregated silica sols which may be used are in commerce for example under the designation "NALCO COLLOIDAL SILICAS" (Nalco Chemical Co.), "Ludox colloidal silica" (Grace) or "Highlink OG" (Clariant).

Submicron fillers or microfillers consisting of agglomerated nanoscale particles may likewise be used, particularly when their specific surface area (determined according to Brunauer, Emmet, Teller) is in the range between 100 to 400 m²/g. Fumed silica or wet-precipitated silica is preferred. Suitable non-surface-treated silicon dioxide filler products that may be used are available commercially under the designations AEROSIL™ ("OX50", "90", "130", "150", "200", "300" and "380", "R8200" from Evonik Industries AG, Essen, Germany), Cab-O-Sil ("LM-150", "M-5", "H-5", "EH-5" from Cabot Corp., Tuscola, IL), HDK™ ("S13", "V15", "N20", "T30", "T40" Wacker-Chemie AG, Munich, Germany) and Orisilt™ ("200", "300", "380" Orisil, Lviv, Ukraine).

Particularly advantageous abrasion resistance and gloss stability properties may be realized in the dental material through the use of aggregated nanoscale particles based on mixed oxides of silicon dioxide and zirconium dioxide. A suitable filler may be produced by a process described for example in U.S. Pat. No. 6,730,156 (Example A). The filler thus produced may then be surface-treated by a process as described in U.S. Pat. No. 6,730,156 (e.g. preparation example B).

Particularly advantageous for attaining high levels of filling in conjunction with high esthetics and abrasion stability may be the use of spherical submicroparticles based on silicon zirconium mixed oxides, as described in DE 19524362 A1 or US2020/0121564 A1.

The aggregated fillers preferably have a mean secondary particle size of 1-15 µm, preferably a mean secondary particle size of 1-10 µm and more preferably a mean secondary particle size of 2-5 µm.

Also present may be significant amounts of selected X-ray-opaque fillers. The addition of X-ray-visible particles to the dental material is advantageous as it enables distinctions to be made between intact hard tooth substance and the restoration. Suitable X-ray-visible fillers comprise particles of metal oxides, metal fluorides or barium sulfate. Oxides and fluorides of heavy metals having an atomic number of greater than 28 are preferred. The metal oxides and fluorides ought to be selected such that they have very little effect on the color of the restoration. More-suitable metal oxides and fluorides are those having an atomic number of greater than 30. Suitable metal oxides are oxides of yttrium, strontium, barium, zirconium, hafnium, niobium, tantalum, tungsten, bismuth, molybdenum, tin, zinc, lanthanides (elements having an atomic number of 57 to 71), cerium and combinations thereof. Suitable metal fluorides are, for example, yttrium trifluoride and ytterbium trifluoride. Of particularly preferred suitability here are irregularly shaped or spherical $YbF_3$ or $YF_3$ particles having a mean primary particle size of 40 nm to 1.5 µm and particular preference is given to core-shell combination products composed of $YF_3$ or $YbF_3$ core and $SiO_2$ shell; with very particular preference, the surface of the $SiO_2$ shell is silanized. In particular, a core-shell combination product of this kind has a refractive index of 1.48 to 1.54 and a measured mean agglomerated particle size of between 0.5 and 5 µm.

Examples of suitable organic fillers are filled and unfilled, pulverized polymers or copolymers based on polymethyl methacrylate (PMMA), polyethyl methacrylate, polypropyl methacrylate, polybutyl methacrylate, (PBMA), polyvinyl acetate (PVAc), polyethylene glycol (PEG), polypropylene glycol (PPG), polyvinyl alcohol (PVA), polyurethanes (PU), polyurea, methyl methacrylate-ethyl methylacrylate copolymer, ethylene-vinyl acetate copolymer, and styrene-butadiene copolymer. The organic filler may further comprise a biologically active component, a defined pigment, a polymerization initiator, a stabilizer or something comparable, added during the production process. The organic fillers may be used alone or as mixtures.

Advantageous polishing properties in conjunction with a higher level of filling may be achieved in the dental materials if so-called organic-inorganic composite fillers are employed. These fillers may be produced by processing a polymerizable monomer with an inorganic filler to form a paste, then curing the paste by polymerization and subjecting the product to fine grinding before using it as a filler. Microfillers are used preferably here as inorganic filler. After grinding, the fillers preferably have a mean particle size of 0.05-100 µm, preferably a mean particle size of 0.5-50 µm and more preferably a mean particle size of 1-30 µm.

It is preferable for the fillers in the dental materials to be surface-modified. For this purpose, for example, the inorganic or organic-inorganic composite fillers described, before being used, are subjected to surface treatment to improve compatibility, affinity and the capacity for incorporation of the fillers into the resin mixture. This treatment provides the surfaces of the inorganic particles with organic modification, meaning that the surfaces exhibit organic structural elements. In this context, all of the processes known to the skilled person can be employed. Silanizing agents are preferred for the inorganic fillers which carry OH groups on the surface. Examples here include γ-methacryloxyalkyltrimethoxysilanes (number of carbon atoms between the methacryloxy group and the silicon atom: 3 to 12), γ-methacryloxyalkyltriethoxysilanes (number of carbon atoms between the methacryloxy group and the silicon atom: 3 to 12) or silicone compounds such as vinyltrimethoxysilane, vinylethoxysilane and vinyltriacetoxysilane. A particularly preferred silanizing agent is methacryloxypropyltrimethoxysilane.

Inorganic fillers with few or no OH groups on the surface are preferably surface-treated with different surface-modifying agents, such as, for example, titanates, aluminates, zircoaluminates, surfactants, fatty acids, organic acids, inorganic acids or metal alkoxides. Particularly preferred surface modification agents for salts of barium, strontium and rare earth metals are organic compounds which carry N—, P—, S—and/or O-containing functional groups (e.g. polyols, sulfoxides, phosphinic esters, phosphonic esters, trialkylphosphines, carboxylic acids and carboxylic esters). Of particular suitability here is 10-methacryloyloxydecyl dihydrogenphosphate.

Particularly in the case of silicon dioxide-based agglomerated nanofillers, the surface modifications may comprise radically reactive groups, such as the aforementioned methacryloyloxyalkyl groups, or else radically unreactive groups. Suitable unreactive groups are, for example, trimethylsilyl, dimethylsilylene or methylsilylidene groups, which may be applied to the surface by silanization for example with hexamethyldisilazane, dimethyldimethoxysilane or methyltrimethoxysilane, respectively. Suitable unreactively surface-modified agglomerated nanofillers are available commercially for example under the designations Aerosil R8200, Aerosil R812S, Aerosil R805, Aerosil R202, Aerosil R974 (Evonik Industries A G, Essen, Germany) or HDKH2000, HDKH200/4 (Wacker Chemie, Burghausen, Germany). With further preference, the agglomerated nanofillers may be modified with groups that are reactive in radical processes, as for example methacryloyl groups. A commercial radically reactively modified agglomerated nanofiller product is available under the designation Aerosil R7200 (Evonik Industries AG, Essen, Germany).

The agglomerated nanofillers may preferably be in largely deagglomerated form, as is described for example in EP1720206.

A dental material of the invention may contain a fraction of filler particles of between 0% and 95% by weight, preferably of 1% to 95% by weight, based on the total mass of the polymerizable dental material. The amount of the filler fraction is chosen in line with the indication for the dental product. For instance, filler amounts as high as possible are used for non-sagging, modelable filling composites, for dental compositions for production of inlays, onlays or overlays, and for compositions for producing dental CAD-CAM materials. In general, these compositions have filler contents of 75% by weight up to 92% by weight, based on the overall composition. Flowable dental composites, securing composites, core buildup materials, crown materials and bridge materials generally have a medium filler range from 40% to 80% by weight, based on the overall composition, whereas for dental varnishes, dental sealing materials, dental infiltrants or dental adhesives, fillers are used in the range from 1% to 40% by weight, based on the overall composition. The filler ranges indicated above should be understood only as guideline values, and may also be departed from according to the fillers selected.

d) Customary Dental Additives

The polymerizable dental material of the invention may comprise further customary dental additives. Customary dental additives are known to the skilled person; preferred additives are inhibitors, stabilizers, accelerators, dyes, fluoridating agents, remineralizing agents, X-ray opacity agents and film-formers.

The purpose of inhibitors and stabilizers is in particular to prevent premature polymerization. These are substances which react with reactive radicals to give more stable scavenger products. Adding inhibitors/stabilizers improves the storage stability of the compositions yet to be cured. In addition, inhibitors may serve to bring the working time of hardening systems into a suitable range. Examples of suitable inhibitors are phenyl derivatives, such as hydroquinone monomethyl ether (HQME) or 2,6-di-tert-butyl-4-methylphenol (BHT). Further inhibitors, such as tert-butylhydroxyanisole (BHA), 2,2 diphenyl-1-picrylhydrazyl, galvinoxyl and triphenylmethyl radicals, 2,3,6,6-tetramethylpiperidinyl-1-oxyl radicals (TEMPO) and derivatives of TEMPO or phenothiazine and also derivatives of this compound, are described in EP 0783880 B1. Alternative inhibitors can be found in DE 10119831 A1 or in EP 1563821 A1.

Stabilizer in the polymerizable dental material may in particular comprise 2,6-di-tert-butyl-4-methylphenol (BHT).

The dental material of the invention may comprise W stabilizers as a customary dental additive. W stabilizers are employed in particular to stabilize the dental material with respect to degradation or discoloration due to UV radiation. Examples of UV absorbers are 2-hydroxy-4-methoxybenzophenone, phenyl salicylate, 3-(2'-hydroxy-5'-methylphenyl)benzotriazole or diethyl 2,5-dihydroxyterephthalate.

The dental material of the invention may comprise, as a customary dental additive, one or more fluoride donor substances in finely divided, particulate form. Fluoride donor substances may be water-soluble fluorides such as sodium fluoride or amine fluoride. Further suitable fluoride donor substances are sparingly soluble fluorides of main group 2. Fluoride-containing glasses as well are suitable fluoride sources.

Further suitable additives are finely particulate substances which release calcium and/or phosphate and so have a remineralizing effect. Suitable remineralizing substances are calcium phosphate compounds such as hydroxylapatite, brushite, monocalcium phosphate, fluoroapatite, and bioactive glasses such as the glasses identified in DE10111449A1, DE102005053954A1 or U.S. Pat. No. 9,517,186B2.

The dental material of the invention may comprise a colorant or colorant mixture selected from fluorescent dyes, fluorescent pigments, organic color pigments, inorganic color pigments, and mixtures thereof.

A fluorescent colorant or pigment is preferably an organic fluorescent dye or an organic fluorescent pigment, more particularly a non-polymerizable, organic fluorescent colorant optionally comprising arylcarboxylic esters, such as diethyl 2,5-dihydroxyterephthalate, arylcarboxylic acids, coumarin, rhodamine, naphthalene imide or derivatives thereof. Inorganic fluorescent pigments may comprise, for example, $CaAl_4O_7:Mn^{2+}(Ba0.98Eu0.02)$ $MgAl_{10}O_{17}$, $BaMgF_4$: $Eu^{2+}$, Y (1.995) Ce (0.005) $SiO_5$. Color pigments which may be in the dental material of the invention comprise organic pigments and also inorganic pigments, such as N,N'-bis(3,5-xylyl)perylene-3,4:9,10-bis(dicarbimide), copper phthalocyanine, titanate pigment, especially chromium antimony titanate (rutile structure), spinel black, especially pigments based on black iron oxide ($Fe_3O_4$), where iron is partly substituted by chromium and copper or nickel and chromium or manganese, zinc iron chromium spinel brown spinel, $((Zn,Fe)(Fe,Cr)_2O_4)$ cobalt zinc aluminate blue spinel and/or titanium oxide.

The constituents in the dental material may be included in the following mass fractions, based on the total mass of the dental material of the invention:
- the monomer mixture from 1% to 99% by weight, preferably from 20% to 95% by weight;
- the at least one initiator or an initiator system for the radical polymerization from 0% to 5% by weight, preferably from 0.01% to 5% by weight;
- the fillers from 0% to 95% by weight, preferably from 1% to 95% by weight, more preferably from 5% to 85% by weight, more preferably still from 20% to 80% by weight;
- the customary dental additives from 0% to 5% by weight, preferably from 0.001% to 5% by weight.

The dental material preferably contains no compound with a bisphenol A-based structural element.

A further subject of the invention is the dental material of the invention, preferably as claimed in any of claims 11 to 13, for use in a therapeutic method as dental composite, filling, underfilling, securing, core buildup, root canal filling, crown, bridge, restoration and/or prosthesis material.

A subject of the invention, moreover, is also a cured dental material produced from the polymerizable dental material of the invention, more particularly as claimed in any of claims 11 to 13.

The invention is now illustratively described using a number of advantageous embodiments.

EXAMPLES

In the examples, a mixture containing oligoester dimethacrylates and bis(methacryloyloxymethyl)tricyclo-[5.2.1.0/2,6]decane (TCDDMA) was used. The structural formula of the mixture used in the examples, of OEDMA with n=1-4 and TCDDMA with n=0, is depicted below.

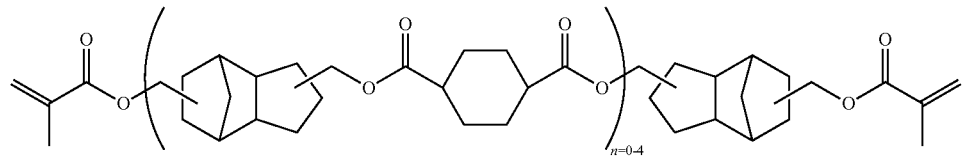

The mixture used may be prepared by esterification reactions, known in the prior art, of tricyclodecanedimethanol with 1,4-cyclohexanedicarboxylic acid and with methacrylic acid.

The mass ratio of the constituents of the mixture of OEDMA and TCDDMA used was analyzed via GPC measurement. This produced a mass fraction of TCDDMA: oligoester n=1: oligoester n=2: oligoester n=3: oligoester n=4 of 31:29:18:16:7. The mass fraction of TCDDMA in the OEDMA mixture was therefore 31% by weight, based on the total mass of the mixture of OEDMA and TCDDMA.

Additionally used were bis(methacryloyloxymethyl)tricyclo[5.2.1.0/2,6]decane, bis(acryloyloxymethyl)tricyclo[5.2.1.0/2,6]decane (TCDDA), 7,7,9-(or 7,9,9-)trimethyl-4,13-dioxo-3,14-dioxa-5,12-diazahexadecane-1,16-diol dimethacrylate (UDMA) and 7,7,9-(or 7,9,9-)trimethyl-4,13-dioxo-3,14-dioxa-5,12-diazahexadecane-1,16-diol diacrylate (UDA), the reaction product of 1 mol of isophorone diisocyanate and 2 mol of 2-hydroxyethyl methacrylate (UDMA-IPDI), triethylene glycol dimethacrylate (TEGDMA), 1,6-hexanediol dimethacrylate (HDDMA) and bisphenol A glycidyl methacrylate (bisGMA).

Preparation of the Resins

In accordance with tables 1 and 2 set out below, monomer mixtures were prepared and an initiator system was added (all figures in % by weight, based in each case on the total masses of the polymerizable dental material). In all of the examples, this system consisted of the same amounts used of camphorquinone (CQ) and 2-ethylhexyl p-(dimethylamino) benzoate (EHA) as co-initiator. 2,6-Di-tert-butyl-4-methylphenol (BHT) was used in all of the mixtures as a stabilizer in the same concentration. The resulting resins were homogenized overnight by magnetic stirrer.

TABLE 1

Composition, volume shrinkage, flexural strength and elasticity modulus of non-inventive dental material compositions

|  |  | Ex. 1 | Ex. 2 | Ex. 3 | Ex. 4 |
|---|---|---|---|---|---|
| OEDMA | % by weight |  |  |  |  |
| TCDDMA |  |  | 74.5 |  | 19.5 |
| UDMA |  |  | 18.7 | 77.9 | 77.9 |
| BisGMA |  | 68.2 |  |  |  |
| TEGDMA |  | 29.2 | 4.2 | 19.5 |  |
| CQ |  | 1.0 | 1.0 | 1.0 | 1.0 |
| EHA |  | 1.598 | 1.598 | 1.598 | 1.598 |
| BHT |  | 0.002 | 0.002 | 0.002 | 0.002 |
| Total |  | 100 | 100 | 100 | 100 |
| Base monomer M1 |  | 0 | 0 | 0 | 0 |
| Base monomer M2 |  | 0 | 74.5 | 0 | 19.5 |
| Base monomer M3 |  | 0 | 18.7 | 77.9 | 77.9 |
| Other monomers |  | 97.4 | 4.2 | 19.5 | 0 |
| Initiator, stabilizer |  | 2.6 | 2.6 | 2.6 | 2.6 |

TABLE 1-continued

Composition, volume shrinkage, flexural strength and elasticity modulus of non-inventive dental material compositions

|  |  | Ex. 1 | Ex. 2 | Ex. 3 | Ex. 4 |
|---|---|---|---|---|---|
| Volume shrinkage | [%] | 6.4 ± 0.3 | 7.0 ± 0.6 | 6.9 ± 0.2 | 6.9 ± 0.3 |
| Flexural strength | [MPa] | 105 ± 8 | 102 ± 4 | 74 ± 5 | 94 ± 6 |
| Elasticity modulus | [GPa] | 2.6 ± 0.1 | 2.4 ± 0.1 | 2.3 ± 0.1 | 2.5 ± 0.1 |

Examples 1 to 4 show, for comparison, the properties of prior-art monomer mixtures. Comparative example 3 corresponds to a polymerizable dental material containing a monomer mixture of EP 2436365 B1.

TABLE 2

Composition, volume shrinkage and flexural strength and elasticity modulus of inventive dental material compositions

|  |  | Ex. 5 | Ex. 6 | Ex. 7 | Ex. 8 | Ex. 9 |
|---|---|---|---|---|---|---|
| OEDMA (containing 31% by weight TCDDMA) | % by weight | 64.3 | 64.3 | 55.0 | 43.8 | 68.2 |
| TCDDMA |  | 23.4 |  | 19.5 |  |  |
| TCDDA |  |  | 23.4 |  | 26.3 | 29.2 |
| UDMA |  | 9.7 |  | 18.7 |  |  |
| UDA |  |  | 9.7 |  | 27.3 |  |
| TEGDMA |  |  |  | 4.2 |  |  |
| CQ |  | 1.0 | 1.0 | 1.0 | 1.0 | 1.0 |
| EHA |  | 1.598 | 1.598 | 1.598 | 1.598 | 1.598 |
| BHT |  | 0.002 | 0.002 | 0.002 | 0.002 | 0.002 |
| Total |  | 100 | 100 | 100 | 100 | 100 |
| Base monomer M1 |  | 44.4 | 44.4 | 38.0 | 30.2 | 47.1 |
| Base monomer M2 |  | 43.3 | 43.3 | 36.5 | 39.9 | 50.3 |
| Base monomer M3 |  | 9.7 | 9.7 | 18.7 | 27.3 | 0 |
| Other monomers |  | 0 | 0 | 4.2 | 0 | 0 |
| Initiator, stabilizer |  | 2.6 | 2.6 | 2.6 | 2.6 | 2.6 |
| Volume shrinkage | [%] | 4.8 ± 0.1 | 4.8 ± 0.2 | 5.8 ± 0.6 | 4.8 ± 0.1 | 4.9 ± 0.2 |
| Flexural strength | [MPa] | 90 ± 4 | 101 ± 5 | 92 ± 4 | 111 ± 3 | 105 ± 5 |
| Elasticity modulus | [GPa] | 2.6 ± 0.1 | 2.6 ± 0.1 | 2.5 ± 0.1 | 2.6 ± 0.1 | 2.7 ± 0.1 |

Examples 5 to 9 correspond to inventive polymerizable dental materials. In example 7, volume shrinkage and flexural strength are markedly improved. Examples 5 and 6 show that the volume shrinkage is further reduced and good flexural strengths were likewise obtained.

Production of the Dental Composites

Dental composites were produced in accordance with tables 3 and 4 set out below. For the production of dental composites, a total of 75% by weight of the dental glass G018-053 from SCHOTT AG (mean particle size 0.7 μm, 6% by weight silane) was added successively to the resins obtained beforehand, based on the total mass fraction of the dental composite, and the mixture was homogenized using a Speedmixer (from Hauschild). The composites were then degassed.

TABLE 3

Composition, volume shrinkage, flexural strength and elasticity modulus of the non-inventive dental composites K-1 and K-2

|  |  | K-1 | K-2 |
|---|---|---|---|
| Resin [% by weight] | Ex. 2 | 25 |  |
|  | Ex. 4 |  | 25 |
| Filler [% by weight] | Dental glass | 75 | 75 |
| Volume shrinkage [%] |  | 2.9 ± 0.2 | 3.0 ± 0.2 |
| Flexural strength [MPa] |  | 126 ± 8 | 144 ± 7 |
| Elasticity modulus [GPa] |  | 9.7 ± 0.5 | 10.1 ± 0.4 |

TABLE 4

Composition, volume shrinkage, flexural strength and elasticity modulus of the inventive dental composites K-3 and K-4

|  |  | K-3 | K-4 |
|---|---|---|---|
| Resin [% by weight] | Ex. 6 | 25 |  |
|  | Ex. 8 |  | 25 |
| Filler [% by weight] | Dental glass | 75 | 75 |
| Volume shrinkage [%] |  | 2.1 ± 0.2 | 2.2 ± 0.4 |
| Flexural strength [MPa] |  | 142 ± 18 | 130 ± 9 |
| Elasticity modulus [GPa] |  | 10.9 ± 0.6 | 10.7 ± 0.3 |

Determination of Flexural Strength and of Elasticity Modulus

Flexural strength and elasticity modulus were determined. For this purpose, test specimens were produced in accordance with ISO 4049:2009. The test specimens were produced by exposure using a HiLite® power photopolymerization apparatus (from Heraeus). For this purpose, the dental composites were exposed in the test specimen molds (40 mm×2 mm×2 mm) for 90 s each from both sides. The test specimens were stored for 24 hours in distilled water at 37° C. The flexural strength and the elasticity modulus were determined using a Zwick universal testing machine. The mean value from 6 individual measurements is reported, along with the standard deviation.

Volume Shrinkage

The volume shrinkage was calculated from the difference in the density p of the dental composites before (VA) and 24 hours after (NA) curing. For each composite, 3 samples were measured; the mean value was used as the density. For density determination of the composites after curing, cylindrical test specimens (8 mm diameter and 2 mm height) were produced by exposure using a HiLite power photopolymerization apparatus (from Heraeus). Exposure took place for 90 s from both sides of the test specimen. The specimens underwent dry storage at 23° C.; for 24 hours. The density of the cured and uncured composites was measured using a helium gas pycnometer (Accupyc III 1340).

The volume shrinkage VS was given by the following formula:

$$VS = 100\% \times (\rho_{NA} - \rho_{VA})/\rho_{NA}.$$

Dynamic Viscosity (Shear Rates)

The dynamic viscosity was measured by means of a Kinexus DSR from Malvern Instruments Ltd. Measurement took place using a plate/plate geometry with a top-plate diameter of 25 mm and a gap width of 0.1 mm. During measurement, a shear stress range from 1 Pa to 50 Pa was traversed. The reading at 50 Pa shear stress was employed for the evaluation. The measurement was made at a constant sample temperature of 23° C., monitored and kept constant by the internal temperature conditioning of the instrument.

GPC Measurement

The GPC was measured on a GPC system (PSS SECcurity GPC System, from PSS Polymer Standards Service GmbH) with column oven and RI detector. The column combination used to separate the constituents was as follows: Pre-column VA 50/7.7 Nucleogel GP 5 P, separating columns VA 300/7.7 Nucleogel GPC 104-5 and VA 300/7.7 Nucleogel GPC 500-5 (all from Macherey & Nagel). The columns were thermostated at 20° C. The sample concentration was 1%. 20 μl of sample were injected and the eluent used was THE (Merck 109731). The flow rate of the eluent was 0.5 ml/min.

The subject matter of the disclosure further includes the additional aspects as well, which have an intrinsic inventive content even without a specific mass ratio Y=m(M2)/m(M1) of the base monomers M2 to M1 of 0.9≤Y≤20, preferably 0.9≤Y≤10, more preferably 0.95≤Y≤3. The further aspects of the disclosure are set out in the form of clauses (in the sense of Decision J15/81 of the Legal Boards of Appeal of the EPO) below:

Clause 1. A monomer mixture for producing a dental material, comprising:

a. at least one base monomer M1 of the following formula 1:

(formula 1)

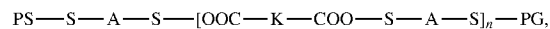
PS—S—A—S—[OOC—K—COO—S—A—S]$_n$—PG, where

PG=a polymerizable group selected from OOC—CH=CH$_2$ and —OOC—C(CH$_3$)=CH;

S=a spacer group selected from unbranched and branched alkylene with C1-C10 carbon atoms that may additionally contain oxygen or —OOC— in the carbon chain, preferably methylene, or S is absent;

A=an aliphatic polycyclic group, preferably an aliphatic tricyclic hydrocarbon group, in which one or more hydrogen atoms may be replaced each independently of one another by C1-C4 alkyl radicals, C1-C4 alkoxy radicals, fluorine atoms, chlorine atoms or trifluoromethyl groups, more preferably tricyclodecanylene, more preferably still tricyclo[5.2.1.0/2,6]decanylene;

K=an aliphatic acyclic or cyclic, saturated or unsaturated unit with C1-C10 hydrocarbon atoms, preferably with C3-C10 hydrocarbon atoms, more preferably a saturated cycloaliphatic unit, more preferably still 1,4-cyclohexanylene;

n=1-9, preferably 1-5, more preferably 1-4;

b. at least one base monomer M2 of the following formula 2:

(formula 2)
PG'—S'—A'—S'—PG', where

PG'=a polymerizable group selected from OOC—CH=CH$_2$ and —OOC—C(CH$_3$)=CH;

S'=a spacer group selected from unbranched and branched alkylene with C1-C10 carbon atoms that may additionally contain oxygen or —OOC— in the carbon chain, preferably methylene, or S' is absent;

A'=an aliphatic polycyclic group, an aliphatic tricyclic hydrocarbon group, in which one or more hydrogen atoms may be replaced each independently of one another by C1-C4 alkyl radicals, C1-C4 alkoxy radicals, fluorine atoms, chlorine atoms or trifluoromethyl groups, more preferably tricyclodecanylene, more preferably still tricyclo[5.2.1.0/2,6]decanylene.

Clause 2. The monomer mixture according to clause 1, characterized in that in the monomer mixture there are two or more base monomers M1, preferably at least two base monomers M2, more preferably more than two base monomers M1, more preferably still more than three base monomers M1, even more preferably still more than four base monomers M1.

Clause 3. The monomer mixture according to clause 1 or 2, characterized in that the base monomer M2 is selected from bis(methacryloyloxymethyl)tricyclo[5.2.1.0/2,6]decane, bis(acryloyloxymethyl)tricyclo[5.2.1.0/2,6]decane and mixtures thereof, the base monomer M2 preferably being bis(methacryloyloxymethyl)tricyclo[5.2.1.0/2,6]decane.

Clause 4. The monomer mixture according to any of clauses 1 to 3, characterized in that the monomer mixture comprises a base monomer M3 which differs from the base monomers M1 of the formula 1 and M2 of the formula 2.

Clause 5. The monomer mixture according to clause 4, characterized in that the base monomer M3 is selected from urethane-based monomers, preferably selected from difunctional urethane (meth)acrylates, polyfunctional urethane (meth)acrylates and mixtures thereof, more preferably urethane di(meth)acrylates, more preferably still urethane di(meth)acrylates selected from linear or branched alkylene-functionalized urethane di(meth)acrylates and urethane di(meth)acrylate-functionalized polyethers.

Clause 6. The monomer mixture according to clause 4 or 5, characterized in that the base monomer M3 is selected from 7,7,9-trimethyl-4,13-dioxo-3,14-dioxa-5,12-diazahexadecane-1,16-diyl bis(2-methylacrylate), 7,9,9-trimethyl-4,13-dioxo-3,14-dioxa-5,12-diazahexadecane-1,16-diyl bis(2-methylacrylate), 7,7,9-trimethyl-4,13-dioxo-3,14-dioxa-5,12-diazahexadecane-1,16-diol diacrylate, 7,9,9- trimethyl-4,13-dioxo-3,14-dioxa-5,12-diazahexadecane-1, 16-diol diacrylate and mixtures thereof.

Clause 7. The monomer mixture according to any of clauses 1 to 6, characterized in that the base monomers may each be included in the following mass fractions, based on the total mass of the monomer mixture:
base monomer M1 from 2% to 52.5% by weight, preferably from 5% to 52.5% by weight, more preferably from 12.5% to 52.5% by weight;
base monomer M2 from 23% to 96% by weight, preferably from 47.5% to 95.5% by weight, more preferably from 47.5% to 87.5% by weight;
base monomer M3 from 0% to 50% by weight, preferably from 0.1% to 30% by weight, more preferably from 1% to 15% by weight.

Clause 8. The monomer mixture according to any of clauses 1 to 7, characterized in that the monomer mixture comprises or consists of the base monomers M1 and M2 in a mass fraction of 25% by weight or more, more preferably of 50% by weight or more, even more preferably of 70% by weight or more, further preferably of 85% by weight or more, more preferably still of 100% by weight, based on the total masses of the monomer mixture.

Clause 9. The monomer mixture according to any of clauses 1 to 8, characterized in that the monomer mixture comprises or consists of the base monomers M1, M2 and optionally M3 in a mass fraction of 95% to 100% by weight, preferably of 99% to 100% by weight, more preferably 100% by weight, based on the total mass of the monomer mixture.

Clause 10. The monomer mixture according to any of clauses 1 to 9, characterized in that in the monomer mixture there is no monomer included that has a bisphenol A structure, preferably no 2,2-bis[4-(2-hydroxy-3-(meth)acryloxypropoxy)phenyl]propane (bisGMA) and no ethoxylated bisphenol A di(meth)acrylate (bisEMA) is included.

Clause 11. The monomer mixture according to any of clauses 1 to 10, characterized in that in the monomer mixture there is no monomer selected from low molecular weight and low-viscosity mono- and di(meth)acrylates, preferably no monomer having a viscosity at a temperature of 23° C.; of less than 0.05 Pa s and/or having a partial water solubility.

Clause 12. The monomer mixture according to any of clauses 1 to 11, characterized in that the monomer mixture is free from hexanediol diacrylate (HDDA), hexanediol dimethacrylate (HDDMA), triethylene glycol diacrylate (TEGDA) and/or triethylene glycol dimethacrylate (TEGDMA).

Clause 13. The monomer mixture according to any of clauses 1 to 12, characterized in that the monomer mixture at a temperature of 23° C.; has a viscosity of 0.2 to 10, preferably 1 to 6, Pa s.

Clause 14. The use of the monomer mixture according to any of clauses 1 to 13 for producing a radically polymerizable dental material, preferably a dental composite, core buildup, root canal filling, filling, underfilling, securing, crown, bridge, restoration and/or prosthesis material.

Clause 15. A polymerizable dental material, comprising:
a) the monomer mixture according to any of clauses 1 to 13;
b) optionally, at least one initiator or an initiator system for the radical polymerization;
c) optionally, fillers;
d) optionally, customary dental additives.

Clause 16. The dental material according to clause 15, characterized in that the constituents may be included in the dental material in the following mass fractions, based on the total mass of the dental material:
a) the monomer mixture from 1% to 99% by weight, preferably from 20% to 95% by weight;
b) the at least one initiator or an initiator system for the radical polymerization from 0% to 5% by weight, preferably from 0.01% to 5% by weight;
c) the fillers from 0% to 95% by weight, preferably from 1% to 95% by weight, more preferably from 1% to 85% by weight, more preferably still from 20% to 80% by weight;
d) the customary dental additives from 0% to 5% by weight, preferably from 0.001% to 5% by weight.

Clause 17. The dental material according to either of clauses 15 and 16 for use in a therapeutic method as dental composite, filling, underfilling, securing, core buildup, root canal filling, crown, bridge, restoration and/or prosthesis material.

Clause 18. The dental material according to any of clauses 15 to 17, characterized in that the dental material is cured thermally, chemically and/or photochemically, preferably by W and/or visible light.

Clause 19. The dental material according to any of clauses 15 to 18, characterized in that the dental material is light-curable.

Clause 20. The dental material according to any of clauses 15 to 19, characterized in that the dental material comprises camphorquinone (CQ) as initiator and 2-ethylhexyl p-(dimethylamino)benzoate (EHA) as co-initiator.

Clause 21. The dental material according to any of clauses 15 to 20, characterized in that the dental material contains no bisphenol-containing compound, preferably no compound having a bisphenol A-based structural element.

Clause 22. A cured dental material produced from a polymerizable dental material according to any of clauses 15 to 21.

The invention claimed is:

1. A monomer mixture for producing a dental material, comprising:
a. at least one base monomer M1 of the following formula 1:

(formula 1)

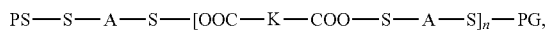

PS—S—A—S—[OOC—K—COO—S—A—S]$_n$—PG, where
PG=a polymerizable group selected from OOC—CH=CH$_2$ and —OOC—C(CH$_3$)—CH$_2$;
S=a spacer group selected from unbranched and branched alkylene with C1-C10 carbon atoms that may additionally contain oxygen or —OOC—in the carbon chain, or S is absent;
A=an aliphatic polycyclic group in which one or more hydrogen atoms may be replaced each independently of one another by C1-C4 alkyl radicals, C1-C4 alkoxy radicals, fluorine atoms, chlorine atoms or trifluoromethyl groups;
K=an aliphatic acyclic or cyclic, saturated or unsaturated unit with C1-C10 hydrocarbon atoms;
n=1-9;

b. at least one base monomer M2 of the following formula 2:

 (formula 2)

where
PG'=a polymerizable group selected from OOC—CH=CH$_2$ and —OOC—C(CH$_3$)=CH$_2$;
S'=a spacer group selected from unbranched and branched alkylene with C1-C10 carbon atoms that may additionally contain oxygen or —OOC— in the carbon chain, or S' is absent;
A'=an aliphatic polycyclic group in which one or more hydrogen atoms may be replaced each independently of one another by C1-C4 alkyl radicals, C1-C4 alkoxy radicals, fluorine atoms, chlorine atoms or trifluoromethyl groups;
where a mass ratio Y=m(M2)/m(M1) of the base monomers M2 to M1 is 0.9≤Y≤20.

2. The monomer mixture as claimed in claim 1, characterized in that the monomer mixture comprises two or more base monomers M1.

3. The monomer mixture as claimed in claim 1, characterized in that the base monomer M2 is selected from bis(methacryloyloxymethyl)tricyclo[5.2.1.0/2,6]decane, bis(acryloyloxymethyl)tricyclo[5.2.1.0/2,6]decane and mixtures thereof.

4. The monomer mixture as claimed in claim 1, characterized in that the monomer mixture comprises a base monomer M3 which differs from the base monomers M1 of the formula 1 and M2 of the formula 2.

5. The monomer mixture as claimed in claim 4, characterized in that the base monomer M3 is selected from urethane-based monomers.

6. The monomer mixture as claimed in claim 1, characterized in that the base monomers are each included in the following mass fractions, based on the total mass of the monomer mixture:
base monomer M1 from 2% to 52.5% by weight;
base monomer M2 from 23% to 96% by weight;
base monomer M3 from 0% to 50% by weight.

7. The monomer mixture as claimed in claim 1, characterized in that the monomer mixture comprises or consists of the base monomers M1, M2 and optionally M3 in a mass fraction of 95% to 100% by weight, based on the total mass of the monomer mixture.

8. The monomer mixture as claimed in claim 1, characterized in that in the monomer mixture there is no monomer included that has a bisphenol A structure.

9. The monomer mixture as claimed in claim 1, characterized in that in the monomer mixture there is no monomer selected from low molecular weight and low-viscosity mono- and di(meth)acrylates, no monomer having a viscosity at a temperature of 23° C. of less than 0.05 Pas and/or having a partial water solubility, and no monomer selected from hexanediol diacrylate (HDDA), hexanediol dimethacrylate (HDDMA), triethylene glycol diacrylate (TEGDA) and triethylene glycol dimethacrylate (TEGDMA).

10. The monomer mixture as claimed in claim 1, characterized in that the monomer mixture at a temperature of 23° C. has a viscosity of 0.2 to 10 Pa s.

11. A method for producing a dental material, comprising radically polymerizing the monomer mixture as claimed in claim 1.

12. A polymerizable dental material, comprising:
a) the monomer mixture as claimed in claim 1;
b) optionally, at least one initiator or an initiator system for the radical polymerization;
c) optionally, fillers;
d) optionally, customary dental additives.

13. The dental material as claimed in claim 12, characterized in that the constituents may be included in the dental material in the following mass fractions, based on the total mass of the dental material:
a) the monomer mixture from 1% to 99% by weight;
b) the at least one initiator or an initiator system for the radical polymerization from 0% to 5% by weight;
c) the fillers from 0% to 95% by weight;
d) the customary dental additives from 0% to 5% by weight.

14. The dental material as claimed in claim 12 for use in a therapeutic method as dental composite, filling, underfilling, securing, core buildup, root canal filling, crown, bridge, restoration and/or prosthesis material.

15. A cured dental material produced from a polymerizable dental material as claimed in claim 12.

16. The monomer mixture as claimed in claim 1, characterized in that:
S=methylene,
A=tricyclo[5.2.1.0/2,6]decanylene;
K=1,4-cyclohexanylene;
n=1-4;
S'=methylene,
A'=tricyclo[5.2.1.0/2,6]decanylene;
where a mass ratio Y=m(M2)/m(M1) of the base monomers M2 to M1 is 0.95≤Y≤3.

17. The monomer mixture as claimed in claim 2, characterized in that the monomer mixture comprises more than four base monomers M1.

18. The monomer mixture as claimed in claim 5, characterized in that the base monomer M3 preferably is selected from 7,7,9-trimethyl-4,13-dioxo-3,14-dioxa-5,12-diazahexadecane-1,16-diyl bis(2-methylacrylate), 7,9,9-trimethyl-4,13-dioxo-3,14-dioxa-5,12-diazahexadecane-1,16-diyl bis(2-methylacrylate), 7,7,9-trimethyl-4,13-dioxo-3,14-dioxa-5,12-diazahexadecane-1,16-diol diacrylate, 7,9,9-trimethyl-4,13-dioxo-3,14-dioxa-5,12-diazahexadecane-1,16-diol diacrylate and mixtures thereof.

19. The monomer mixture as claimed in claim 6, characterized in that the base monomers are included in the following mass fractions, based on the total mass of the monomer mixture:
base monomer M1 from 12.5% to 52.5% by weight;
base monomer M2 from 47.5% to 87.5% by weight;
base monomer M3 from 1% to 15% by weight.

20. The method of claim 11, wherein the dental material is a dental composite, core buildup, root canal filling, filling, underfilling, securing, crown, bridge, restoration and/or prosthesis material.

* * * * *